Figure 5:
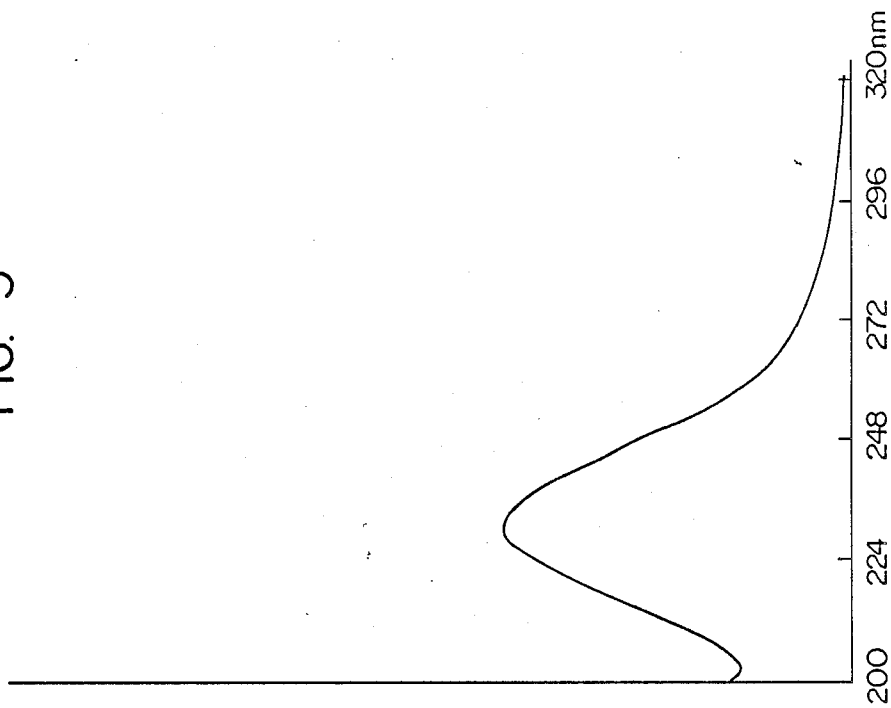

United States Patent [19]

Nakayama et al.

[11] Patent Number: 4,981,954
[45] Date of Patent: Jan. 1, 1991

[54] NOVEL AZOXY COMPOUNDS AND PROCESS FOR PRODUCTION THEREOF

[75] Inventors: Masahito Nakayama, Kodaira; Hisakatsu Ito, Kawagoe; Isamu Watanabe, Higashimurayama; Masami Shiratsuchi, Musashimurayama, all of Japan

[73] Assignee: Kowa Company, Ltd., Aichi, Japan

[21] Appl. No.: 167,242

[22] Filed: Mar. 11, 1988

[30] Foreign Application Priority Data

Mar. 13, 1987 [JP] Japan .................... 62-56494

[51] Int. Cl.$^5$ .................... C07C 283/09
[52] U.S. Cl. .................... 534/566; 514/149; 435/128; 435/253.5; 435/886
[58] Field of Search .................... 534/566; 514/149

[56] References Cited

U.S. PATENT DOCUMENTS 3,647,776 7/1972 McGahren et al. .................... 534/566

OTHER PUBLICATIONS

McGahren et al., "Journal of the American Chemical Society", 92, No. 6, pp. 1587-1590, Mar. 25, 1970.

Primary Examiner—Carolyn S. Elmore
Attorney, Agent, or Firm—Wenderoth, Lind & Ponack

[57] ABSTRACT

Novel azoxy compounds having antifungal activity and being useful for the treatment of mycoses, represented by the following formula

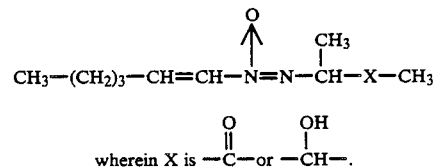

wherein X is $-\overset{O}{\underset{\|}{C}}-$ or $-\overset{OH}{\underset{|}{CH}}-$.

are prepared by culturing a microorganism of Streptomyces sp. (KC-7367, FERM BP-1277) and separating the compounds from the culture broth.

1 Claim, 5 Drawing Sheets

NOVEL AZOXY COMPOUNDS AND PROCESS FOR PRODUCTION THEREOF

This invention relates to novel azoxy compounds suitable for use in the treatment of mycoses.

In recent years, superficial and deep mycoses by various causes have increased worldwide. The number of known chemotherapeutic agents suitable for use in the treatment of mycoses is not few, but there are only four drugs which can be systemically used, namely griseofluvin for trichophytosis which is superficial mycosis, flucytosine, and amphotericin B and miconazole for deep-seated mycosis. Since these systemic drugs have strong sideeffects, they are limited in use, and it has been desired to develop a new type of better systemic antifungal drug.

With a view to developing a new antifungal drug having stronger fungicidal activity on eumycetes, the present inventors have investigated on substances which are produced by microorganisms isolated from the soil, and consequently discovered that a strain (KC-7367) of the genus Strepotomyces which was isolated from the soil in Shimane Prefecture, Japan produces antifungal substances showing strong fungicidal activity on eumycetes. They further succeeded in isolating the above substances from the culture broth of this microorganism strain.

The substances produced by culturing this strain are an azoxy compounds represented by the following formula

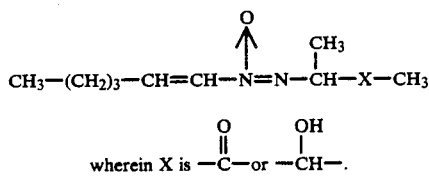

wherein X is $-\overset{O}{\overset{\|}{C}}-$ or $-\overset{OH}{\overset{|}{CH}}-$.

This azoxy compounds can be produced by culturing a microorganism of the genus Streptomyces having the ability to produce these compounds, and isolating the compounds from the culture broth.

These substances are believed to be novel substances because these physical, chemical and biological properties differ from those of known substances. These were named KA-7367A substance

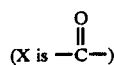

(X is $-\overset{O}{\overset{\|}{C}}-$)

and KA-7367B substance

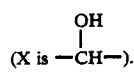

(X is $-\overset{OH}{\overset{|}{CH}}-$).

The KC-7367 strain capable of producing the KA-7367A and KA-7367B substances of this invention was obtained by suspending a soil sample collected at Shinjyo-mura, Shimane Prefecture, Japan in, for example, sterilized water plating the suspension on a medium (pH 7.0) prepared by adding 0.1% of meat extract, 50 μg/ml of mycostatin, 0.4μg/ml of penicillin G, 2 μg/ml of polymixin, 8 μg/ml of nalidixic acid and 1.5% of agar to a potato steep liquor (10% of potato, 0.5% of tomato paste and 1% of oatmeal), culturing it at 27° C. for 7 days, and collecting the resulting colonies The KC-7367 stain has the following microbiological properties. Properties on various media were determined by culturing the strain at 27° C. for 14 days and observing it in a customary manner. The expression of colors was in accordance with the classifications of Color Harmony Manual, 4th edition (Container Corporation of America).

I. Morphological Properties

This strain produces vegetative aerial mycelium in various media. The aerial mycelium branches monopodially with sporephores. The sporephores have 10-50 spores per chain. The spores are cylindrical, 1.1-1.3 x 1.3-1.5 nm in size, with a smooth surface. Flagellated spore, sporangium, selerotium and fragmentation of substratal mycelium were not observed.

II. Cultural Characteristics on Various Culture Media

| 1. | Sucrose-nitrate agar | |
|---|---|---|
| | Growth: | Good |
| | Aerial mycelium: | Poor, white (a) |
| | Substratal mycelium: | Light ivory eggshell (2 ca) |
| | Soluble pigment: | None |
| 2. | Glucose-asparagine agar: | |
| | Growth: | Poor |
| | Aerial mycelium: | Poor, white (a) |
| | Substratal mycelium: | White (a) |
| | Soluble pigment: | None |
| 3. | Glycerol-asparagine agar: | |
| | Growth: | Moderate |
| | Aerial mycelium: | Poor, orchid mist (10 cb) |
| | Substratal mycelium: | Colonial yellow (2 ga) |
| | Soluble pigment: | None |
| 4. | Inorganic salt-starch agar: | |
| | Growth: | Moderate |
| | Aerial mycelium: | Poor, reseda green (24 ig) |
| | Substratal mycelium: | Dark olive (1½ nl) |
| | Soluble pigment: | None |
| 5. | Tyrosine agar: | |
| | Growth: | Good |
| | Aerial mycelium: | Moderate, white (a) to reseda green (24 ig) |
| | Substratal mycelium: | Dark brown (3 nl) |
| | Soluble pigment: | None |
| 6. | Nutrient agar: | |
| | Growth: | Moderate |
| | Aerial mycelium: | Poor, white (a) |
| | Substratal mycelium: | Light yellow (1½ ea) |
| | Soluble pigment: | Squash yellow (2 ia) |
| 7. | Yeast extract-malt extract agar: | |
| | Growth: | Good |
| | Aerial mycelium: | Moderate, reseda green (24 ig) |
| | Substratal mycelium: | beige brown (3 ig) to light melon yellow (3 ea) |
| | Soluble pigment: | Squash yellow (2 ia) |
| 8. | Oatmeal agar: | |
| | Growth: | Moderate |
| | Aerial mycelium: | Moderate, pearl gray (13 dc) |
| | Substratal mycelium: | Dark brown (3 nl) |
| | Soluble pigment: | Nude tan (4 gc) |

III. Physiological Properties

1. Growth temperature range: 18° to 40° C.
Preferable growth temperature range: 26° to 38° C.
2. Liquefaction on gelatin: Negative 3. Hydrolysis of starch: Positive
4. Coagulation of skimmed milk: Negative
   Peptonization of skimmed milk: Positive
5. Formation of melanoid pigment: Negative

IV. Utilization of Carbon Sources

On a Pridham and Gottlieb agar medium, L-arabinose, D-xylose, D-glucose, D-fructose, inositol, L-rhamnose and D-manitrol are utilized, but sucrose and raffinose are not utilized.

V. Cell Wall

L,L-2,6-Diaminopimelic acid was detected in the hydrolysis product of the cell wall.

In view of the foregoing properties, the KC-7367 strain is considered to belong to the genus Strepomyces.

The present inventors named this strain Streptomyces sp. KC-7367, and deposited it on Feb. 4, 1987 in Fermentation Research Institute, Agency of Industrial Science and Technology, 1-3, Higashi 1 chome, Tsukuba-shi, Ibaraki-ken 305, Japan (deposit number No. 1277; FERM BP-1277).

Natural and artificial mutants of the Streptomyces sp. KC-7367, and those microogrganisms which belong to the genus Streptomyces and which have the ability to produce KA-7367 can of course be used in this invention.

Ordinary methods of culturing actinomyceses can be used for culturing the present strain, Streptomyces sp. KC-7367. Various substances can be used as carbon sources of the culture medium, but preferably, starch, glucose, glycerol, maltose, dextrin, sucrose, fructose and molasses are used either singly or in combination. Depending upon the assimilability for the microorganism strain, hydrocarbons, organic acids, and vegetable oils may also be used. Nitrogen sources include, for example, soybean meal, yeast extract, dry yeast, peptone, polypeptone, meat extract, corn steep liquor, casamino acid, distiller's solubles, ammonium chloride, ammonium sulfate, urea and sodium nitrate either singly or in combination. As required, it is possible to add inorganic salts such as sodium chloride, potassium phosphate, magnesium sulfate, calcium chloride, calcium carbonate, calcium hydroxide, cobalt chloride, zinc sulfate, iron chloride and iron sulfate, and very small amounts of metals. Organic and inorganic substances may be added, as desired, in order to aid in the growth of the microorganism and promote production of KA-7367. When the culturing is carried out under aeration, defoamers such as fatty oils, silicone oils, paraffins and surfactants may be used.

The culturing may be carried out on a solid medium. Preferably, however, a liquid culturing method, especially submerged liquid culturing method, is preferably used as in general methods of antibiotic production. The culturing is carried out under aerobic conditions at 20° to 35° C., preferably 25° to 35° C.

Production of KA-7367 substances is effected by shaking culture or tank culture. In either case, after culturing the above microorganism for 1 to 5 days, active substances are produced and accumulated in the culture broth. When the amount of the substances produced in the culture broth reached a maximum, the culturing is stopped, and KA-7367A and KA-7367B are isolated from the culture broth and purified.

KA-7367A and KA-7367B can be isolated in a customary manner, for example by subjecting the culture broth to filtration with a filtration aid, centrifugation, etc. to obtain a culture filtrate, and separating these substances by using an adsorbent or extracting the filtrate with a solvent. In the method using adsorbents, the cultivation filtrate is passed through an adsorbent, for example activated carbon or an adsorbent resin such as Diaion HP-10, HP-20 and HP-50 (products of Mitsubishi Chemical Co., Ltd.) and Amberlite XAD-2, XAD-4 and XAD-7 (products of Rohm & Haas Co.). The adsorbent is then eluted with ethyl acetate, acetone, methanol, ethanol, etc., and the eluate is treated in a customary manner whereby KA-7367A and KA-7367B can be isolated. The solvent extraction method may be carried out in a customary manner by using chloroform, dichloromethane, ethyl acetate, butyl acetate, n-butanol, etc. either alone or in combination.

KA-7367A and KA-7367B may be separated from each other conveniently by using preparative thin-layer chromatography, for example.

The isolated KA-7367A and KA-7367B may further be purified by gel filtration using Sephadex LH-20 (a product of Pharmacia), Toyopearl TSK HW-40 (a product of Toyo Soda Co., Ltd ), etc. adsorption chromatography using silica gel or alumina, high-performance liquid chromatography, etc. These methods may be applied singly or in combination.

The physical, chemical and biological properties of the KA-7367A and KA-7367B substances in accordance with the present invention are shown below.

Figure 1:
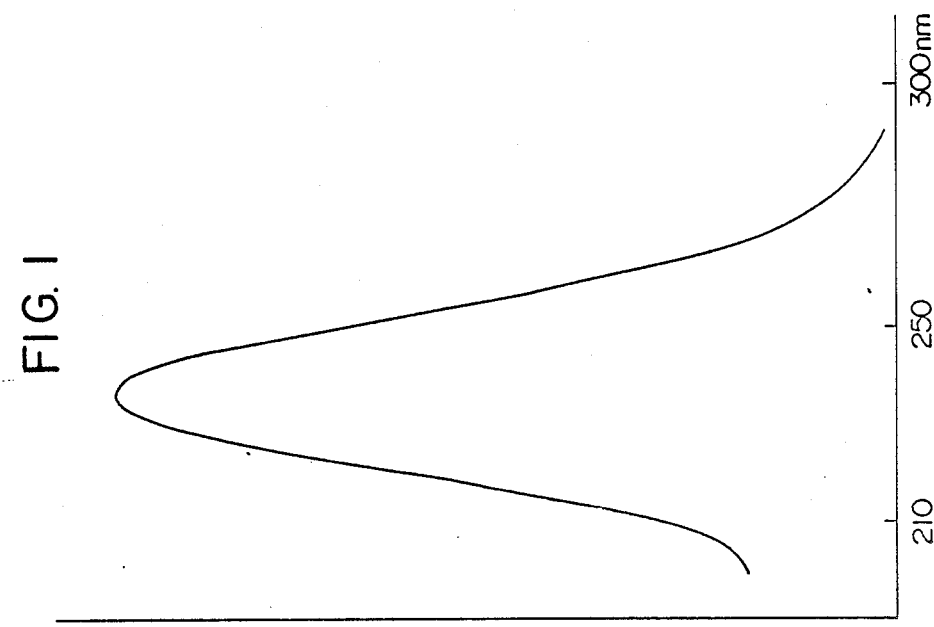
Figure 2:
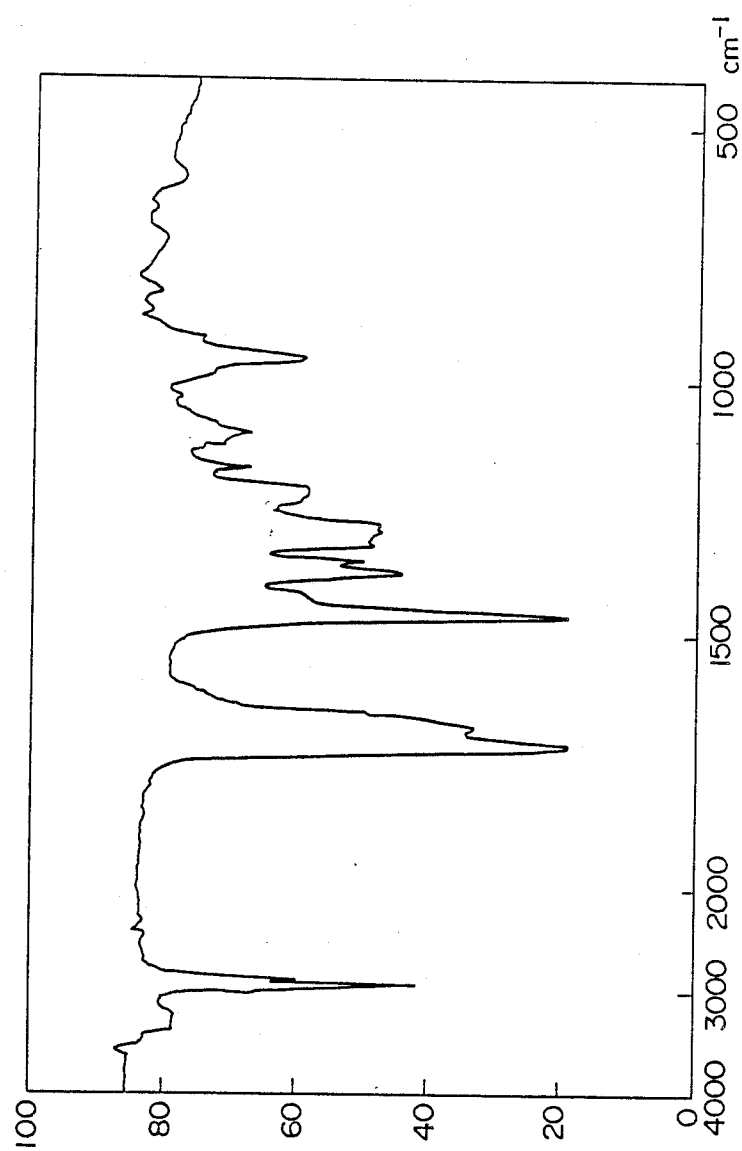
Figure 3:
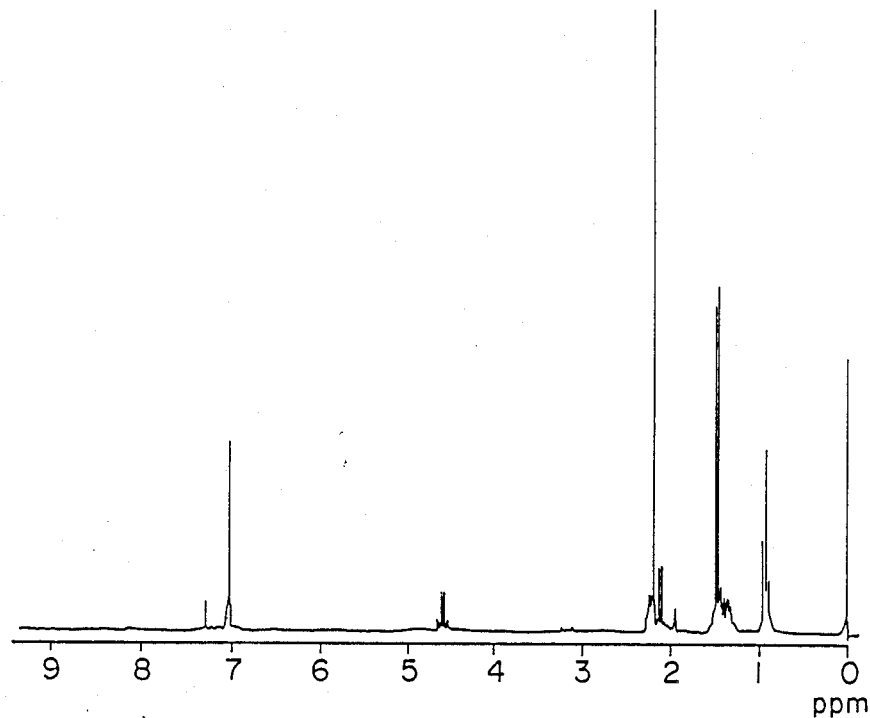
Figure 4:
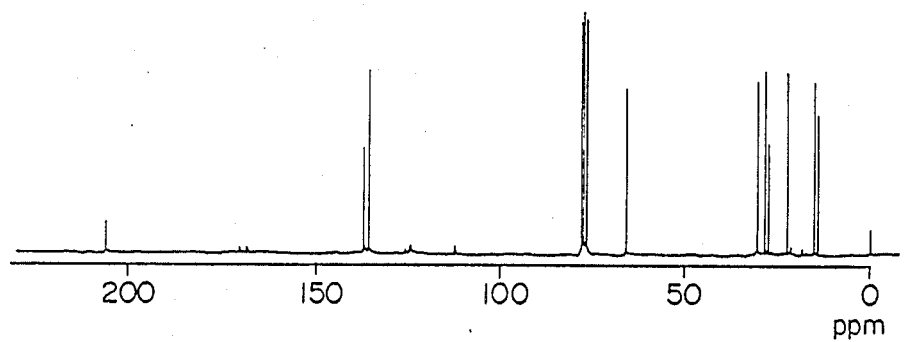
Figure 6:
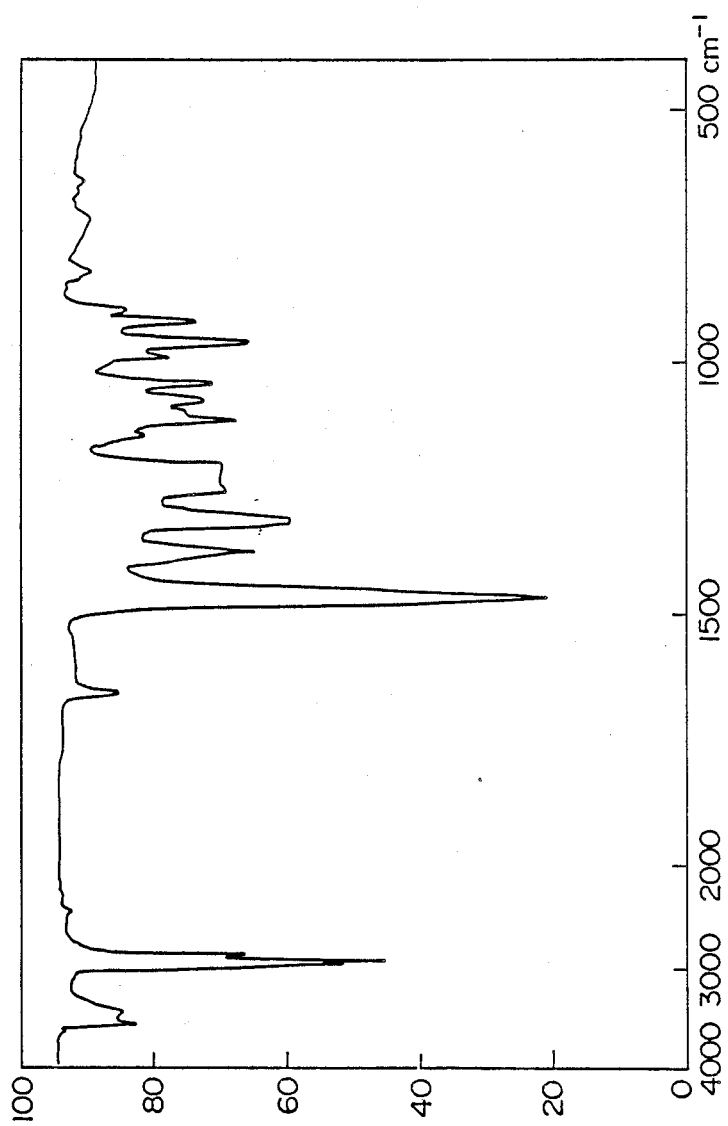
Figure 7:
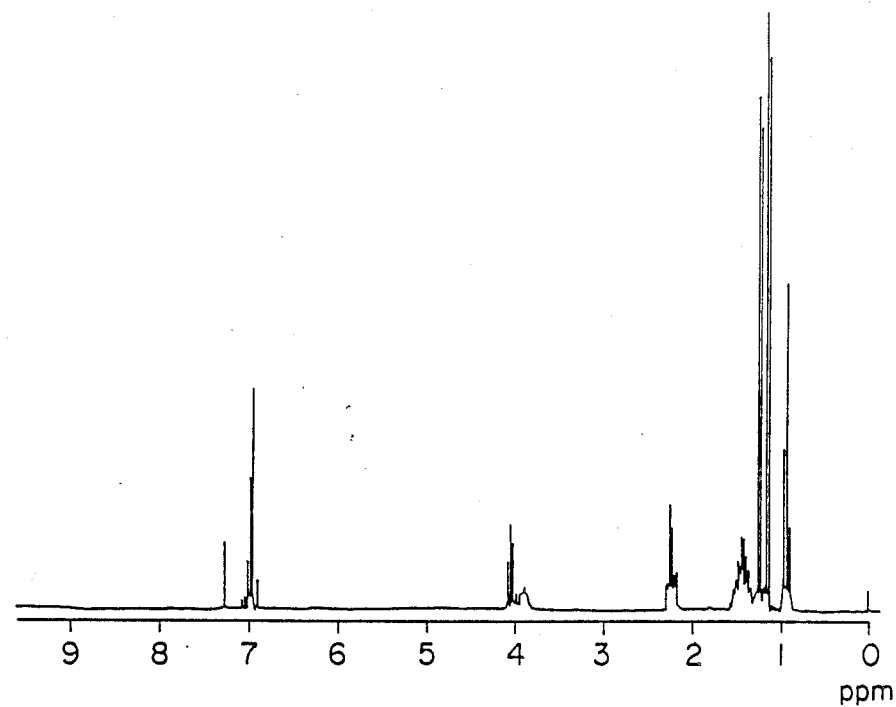
Figure 8:
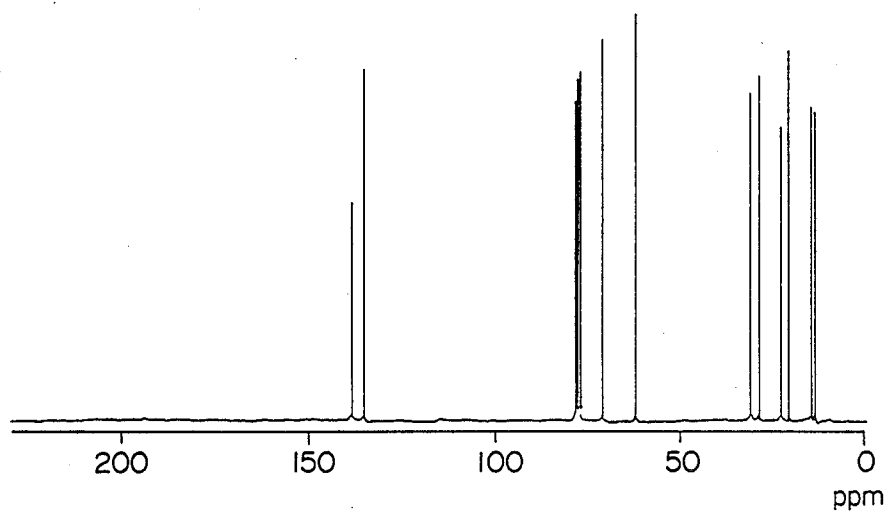

1. Appearance
   Neutral colorless oil (both A and B)
2. Molecular weight
   198 (A), 200 (B)
3. Elemental analyses
   (A) C 60.16%, H 9.12%, N 13.98%
   (B) C 59.95%, H 10.3%, N 13.86%
4. Mass spectra
   (A) m/z 199 (MH$^+$)
   (B) m/z 201.1607 (MH$^+$)
6. Specific rotation $[x]_D^{25}$
   (A) −186° (c O.5, CH$_3$OH)
   (B) +69° (c 1.2, CH$_3$OH)
7. UV absorption spectra
   The UV absorption spectra measured in methanol solution are shown in FIGS. 1 and 5.
   (A) 237 (35300)
   (B) 230 (45000)
8. IR absorption spectra
   The IR absorption spectra measured in chloroform solution are shown in FIGS. 2 and 6.
9. $^1$H-NMR spectra
   The $^1$H-NMR spectra measured in deuterochloroform solution are shown in FIGS. 3 and 7.
10. $^{13}$C-NMR spectra
    The $^{13}$C-NMR spectra measured in deuterochloroform solution are shown in FIGS. 4 and 8.
11. Solubility in solvents
    Both are soluble in chloroform, acetone and methanol, and insoluble in water.
12. Color reaction
    Both are positive in potassium permanganate reaction, and negative in ninhydrin reaction.
13. Thin-layer chromatographies

| Rf | Developing solvent |
    |---|---|
    | (A) 0.53 (B) 0.22 | benzene/ethyl acetate (10:1) |
    | (A) 0.38 (B) 0.28 | chloroform |

Plate : silica gel plate F$_{254}$

-continued

| (Merck & Co.) |
| --- |

14. Structural Formula

From the above physicochemical properties, KA-7367A and KA-7367B are considered to have the following structural formulae.

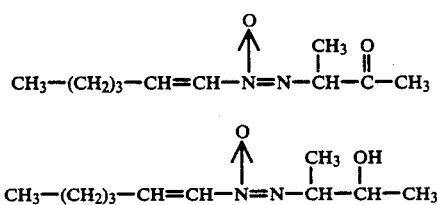

15. Antifungal Activities

The minimum growth inhibition concentrations (MIC) of the present substances against eumycetes are as tabulated below.

| Test microorganism | MIC (μg/ml) | |
| --- | --- | --- |
|  | (A) | (B) |
| Candida albicans | 1.6 | 50 |
| Aspergillus fumigatus | 6.25 | 100 |
| Cryptococcus neoformans | 3.2 | 100 |
| Trichophyton mentagraphytes | 6.25 | 100 |
| Trichophyton rubrum | 3.2 | 100 |
| Culture medium: Sabouraud dextrose agar | | |
| Culturing conditions: 27° C., 2 to 4 days | | |

When the above properties were compared with those of known substances, no agreement was found. Hence, both KA-7367A and KA-7367B were determined to be novel compounds.

In the above properties, the values under (A) are those of KA-7367A, and those under (B) are for KA-7367B. FIGS. 1, 2, 3 and 4 relate to KA-7367A, and FIGS., 5, 6, 7 and 8, to KA-7367B.

KA-7367A and KA-7367B can be chemically converted into each other. Action of a reducing agent on KA-7367A gives KA-7367B, and action of an oxidizing agent on KA-7367B gives KA-7367A.

The reducing agent may be, for example, sodium borohydride, potassium borohydride, lithium borohydride or diborane. The reducing reaction is effected by stirring KA-7367A and 1 to 10 equivalents of the reducing agent in an organic solvent such as alcohols, ethers, hydrocarbons, halogenated hydrocarbons, dimethyl sulfoxide and dimethylformamide at 0° to 100° C. for several minutes to several hours.

The oxidizing agent may be, for example, pyridinium dichromate, pyridinium chlorochromate, chromic acids and manganese dioxide. The oxidation reaction is effected by stirring KA-7367B and 1 to 10 equivalents of the oxidizing agent in an organic solvent such as those mentioned above for 1 hour to several days, preferably in the presence of a catalyst such as pyridinium trifluoroacetate.

The following Examples illustrate the present invention more specifically.

EXAMPLE 1

Streptomyces sp. KC-7367 grown on a potato dextrose agar slant medium was inoculated in a liquid medium (pH 7.5) containing 1% of soluble starch, 1% of glucose, 1% of soybean flour, 0.5% of corn steep liquor, 0.05% of magnesium sulfate heptahydrate, 0.3% of calcium carbonate and 0.0005% of cobalt chloride hexahydrate, and cultured at 28° C. for 2 days to prepare a seed culture.

A 30-liter jar fermentor was charged with 10 liters of a liquid medium (pH 7.5) containing 1% of soluble starch, 0.5% of polypeptone S, 0.2% of yeast extracting, 0.05% of magnesium sulfate heptahydrate, 0.0005% of cobalt chloride hexahydrate and 0.2% of cottonseed oil. 100 ml of the seed culture obtained as above was inoculated in the culture medium, and cultured at 28° C. for 2 days with stirring at 300 rpm while circulating air at a rate of 5 liters/min.

After culturing, the culture broth was filtered, and a filtrate (40 liters) was adsorbed on a column (6 x 70 cm) of Diaion HP-20. The column was washed with a small amount of 50% aqueous methanol and then eluted with methanol. Fractions having antifungal activity on Candida albicans were collected, and concentrated to dryness under reduced pressure. The residue was dissolved in 200 ml of ethyl acetate and washed with 100 ml of a 5% aqueous solution of sodium hydrogen carbonate, 100 ml of 0.02N hydrochloric acid and then with 100 ml of water.

The ethyl acetate layer was concentrated to dryness under reduced pressure. The residue was dissolved in a small amount of methanol, and purified by gel chromatography (column: 2 x 90 cm; developing solvent: methanol) using Toyopearl TSK HW-40. The active fractions were collected and concentrated under reduced pressure. The residue was developed by preparative thin-layer chromatagraphy (developing solvent: benzeneethyl acetate =10:1) using silica gel plate 60 F254 (a product of Merck & Co.). Active fractions having an Rf of 0.53 (KA-7367A) and an Rf of 0.22 (KA-7367B) were collected, and each eluted with ethyl acetate. The eluates were concentrated under reduced pressure. The residue was dissolved in methanol, and purified by gel chromatography (column: 1.5 x 90 cm; developing solvent: methanol) using Sephadex LH-20. The active fractions were collected and concentrated under reduced pressure to give 30 mg of KA-7367A and 3 mg of KA-7367B were obtained as a colorless oil.

EXAMPLE 2

Five hundred milligrams of KA-7367A was dissolved in 10 ml of methanol, and 160 mg of sodium borohydride was added. The mixture was stirred at room temperature for 30 minutes. The reaction mixture was concentrated under reduced pressure The concentrate was dissolved in a mixture of 20 ml of ethyl acetate and 20 ml of water. The ethyl acetate layer was separated, and concentrated to dryness under reduced pressure to give an oily substance. The oily substance was purified by silica gel column chromatography developing solvent: benzene/ethyl acetate (10/1) to give 340 mg of a mixture of KA-7367B and its isomer (in a mixing ratio of about 1:1).

$^1$H-NMR, $\delta CDCl_3$: 1.86 (t), 2.30 (d), 2.37 (d), 2.46 (d).

EXAMPLE 3

KA-7367B (78 mg) was dissolved in 3 ml of methylene chloride, and 37 mg of pyridinium trifluoroacetate and 243 mg of pyridinium dichromate were added. The mixture was stirred at room temperature. Five hours later, 247 mg of pyridinium dichromate was added, and the mixture was further stirred at room temperature for 15 hours. Diethyl ether (20 ml) was added to the reaction mixture, and the solution was suction-filtered by using Celite to remove the impurities. The filtrate was concentrated under reduced pressure to give 101 mg of a crude oily substance. This substance was purified by silica gel column chromatography developing solvent: benzene-ethyl acetate (50:1) to give 19 mg of a colorless oily substance.

The physical, chemical and biological properties of this substance agreed with those of KA-7367A obtained in Example 1.

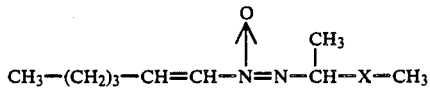

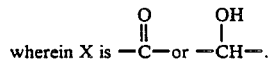

What we claim is:

1. A compound represented by the following formula